United States Patent
Elliott et al.

[11] Patent Number: 6,015,248
[45] Date of Patent: Jan. 18, 2000

[54] WOOD CORER DEVICE

[75] Inventors: Terrence Charles Elliott, Carisbrook; Gary John Nevill, Ballarat; Ian Kenneth Byrne, Maryborough; Anthony Mason Adams, Maryborough; M Lyle Courtney, Maryborough; David Spencer, Campbell, all of Australia

[73] Assignee: Commonwealth Scientific and Industrial Research Organisation, Campbell, Australia

[21] Appl. No.: 09/043,289
[22] PCT Filed: Sep. 19, 1996
[86] PCT No.: PCT/AU96/00587
§ 371 Date: Sep. 1, 1998
§ 102(e) Date: Sep. 1, 1998
[87] PCT Pub. No.: WO97/11346
PCT Pub. Date: Mar. 27, 1997

[30] Foreign Application Priority Data

Sep. 19, 1995 [AU] Australia .................. PN 5525

[51] Int. Cl.⁷ .................. G01N 1/08; B23B 51/04
[52] U.S. Cl. .............. 408/204; 73/864.44; 408/206; 408/703
[58] Field of Search .................. 408/204, 206, 408/703; 73/864.44, 864.45

[56] References Cited

U.S. PATENT DOCUMENTS

| | | | |
|---|---|---|---|
| 715,631 | 12/1902 | Ayres | 73/864.44 |
| 1,162,901 | 12/1915 | Cantey | 73/864.44 |
| 3,110,184 | 11/1963 | Gruetzman | 408/204 |
| 4,696,308 | 9/1987 | Meller et al. | 408/204 |
| 5,433,560 | 7/1995 | Duncan | 408/206 |

FOREIGN PATENT DOCUMENTS

| | | | |
|---|---|---|---|
| 253907 | 4/1961 | Australia . | |
| 0333651 | 9/1989 | European Pat. Off. . | |
| 0420602AZ | 4/1991 | European Pat. Off. . | |
| 106808 | 11/1899 | Germany | 408/204 |
| 1762151 | 9/1992 | U.S.S.R. | 73/864.44 |

*Primary Examiner*—Steven C. Bishop
*Attorney, Agent, or Firm*—Kenyon & Kenyon

[57] ABSTRACT

A wood coring drill bit comprising a hollow tube having an internal bore (103) and an exterior (100) with equally spaced bodies (10) of substantially uniform width extending in a helical manner from a cutting end (10) of said drill bit, said bodies (10) defining equally spaced flutes (15) between the edges of adjacent bodies (10), each body (10) comprising a land (20) upstanding from a relief (21) at the leading edge of the body (10), a respective cutting face (12) and associated lip (25) being formed at the end of each body (10) at said cutting end. The wood coring drill bit is characterized by having three equally spaced bodies (10) and flutes (15) said cutting face (12) has an included angle which is preferably 125° for hardwood and drywood and 112° for softwood. The lip (25) has a lip clearance angle that is about 6°±1°, the lands (20) on the bodies (10) extend for an axial distance of about 65 mm±5 mm from said cutting end (101) and the internal bore (103) of the hollow tube is tapered outwardly from or adjacent the cutting end (101).

18 Claims, 5 Drawing Sheets

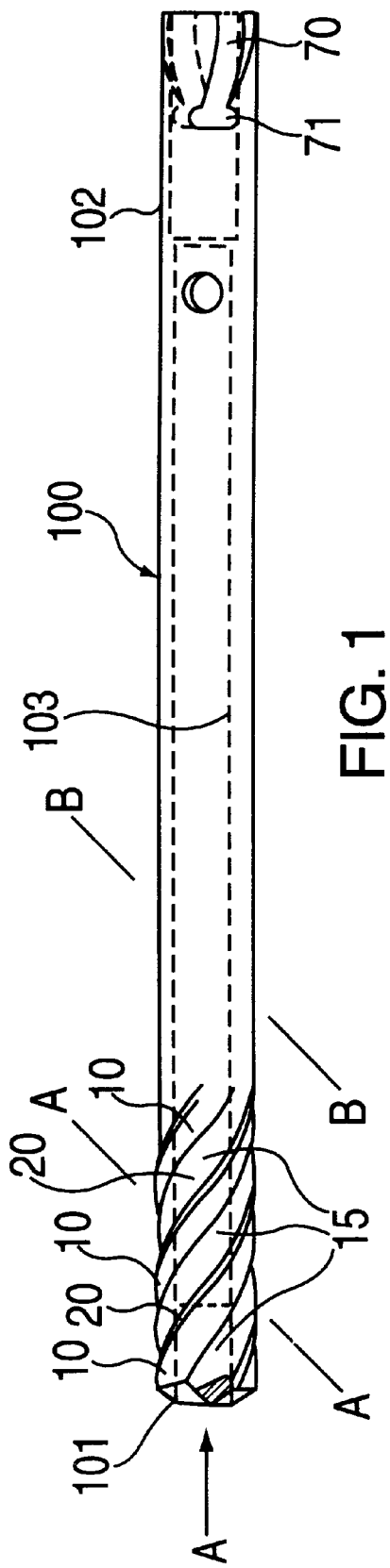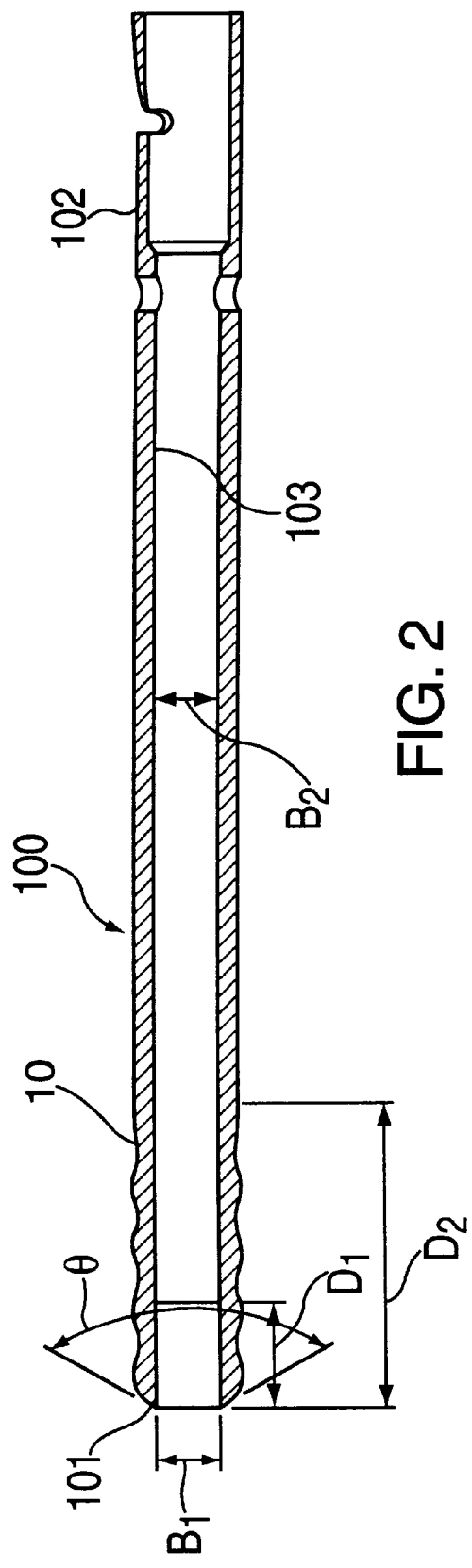

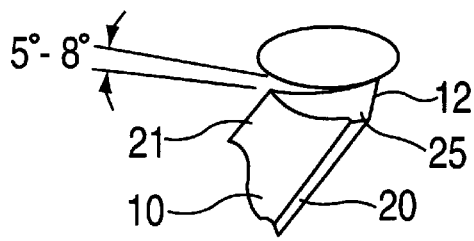
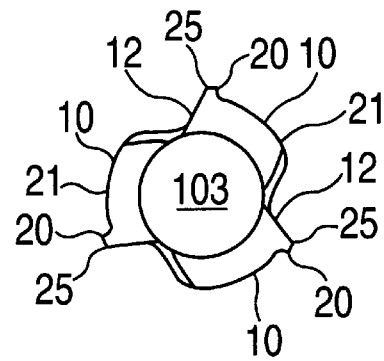
FIG. 3　　　　　　FIG. 4
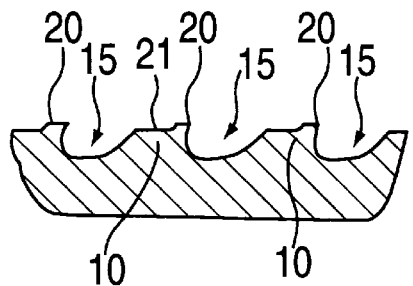
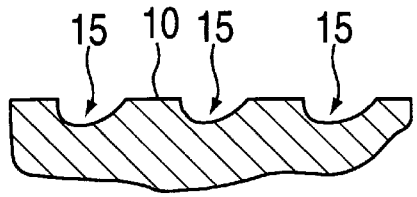
FIG. 5　　　　　　FIG. 6
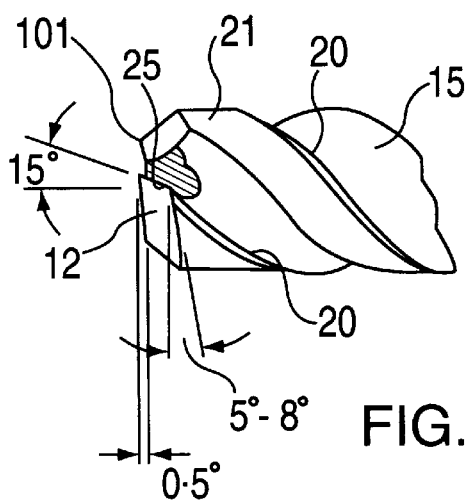
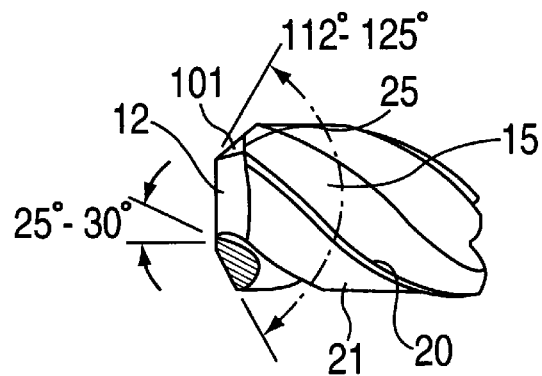
FIG. 7a　　　　　　FIG. 7b

WOOD CORER DEVICE

TECHNICAL FIELD

This invention concerns wood corers. More particularly, it concerns a drill bit for coring wood which comprises a hollow drill bit with helical bodies and flutes which can be adapted for use with a power drill to obtain core samples of wood (for example, trees or telegraph poles).

BACKGROUND TO THE INVENTION

There are many instances in which it is desirable to be able to take a core sample of a timber structure. Forestry workers use such wood cores to evaluate the properties of selected trees—particularly for an analysis of the fibre structure of the tree wood. Electrical power companies and telephone companies use wood cores to test the soundness of the poles on which power and telephone cable are mounted. Structural engineers use core samples of wooden beams, poles and the like to assess the soundness of wooden structures.

A number of devices have previously been used to obtain wood cores. Probably the most popular corer for green wood sampling is a hand-operated tree corer (from Scandinavia) which consists of a hollow steel tube with a tapered spiral external thread on the head. The rotating action cuts the wood fibres on scribes and the cut core slips inside the tube during extraction. The device is operated by quite extreme physical exertion in applying force to a pair of transverse arms extending outwardly from the rear of the T-shaped device. As the corer moves into the tree it compresses the wood tissue around the shaft, rather than removing it, making rotation more difficult the further the corer moves into the tree, particularly when coring wood such as eucalypt which does not compress readily. Risk of muscular injury is therefore quite high. Although this device has the advantages of simple construction and an ability to provide wood cores on soft conifers, it is physically exhausting to use constantly, and extremely difficult to use on hardwood species such as eucalypts.

Another wood corer that has been used in Australia comprises a trepanning head at the end of a long hollow shaft attached to a power drill. This equipment requires a heavy frame, which is clamped to the tree, beam or pole that is being sampled before drilling can commence. In addition to being difficult to transport, it cuts a core with a 25 mm diameter and leaves a hole which has a diameter of 40 mm—which is generally unacceptable from a tree husbandry viewpoint.

There has long been a need for a wood corer which is easy to use and easily transportable, and which cuts a suitable size core quickly, through all species of wood, both green and dry.

SUMMARY OF THE INVENTION

According to the present invention there is provided a wood coring drill bit comprising a hollow tube having a internal bore and an exterior with equally spaced bodies of substantially uniform width extending in a helical manner from a cutting end of said drill bit, said bodies defining equally spaced flutes between the edges of adjacent bodies, each body comprising a land upstanding from a relief at the leading edge of the body, a respective cutting face and associated lip being formed at the end of each body at said cutting end. The tube of the coring drill bit has three equally spaced bodies and flutes, said cutting face has an included angle which is within the range of 106° to 131°, the lip has a lip clearance angle that is about 6°±1°, the lands on the bodies extend for an axial distance of about 65 mm±5 mm from said cutting end and the internal bore of the hollow tube is tapered outwardly from or adjacent the cutting end.

Preferably the outside diameters of the bodies are stepped down by about 0.5±0.1 mm at a distance of about 65 mm±10 mm from said cutting end.

When used on hardwood the included cutting angle is within the range 118° to 131° preferably 125°.

When used on softwood the included cutting angle is within the range 106° to 118° preferably 112°.

When used on drywood the included cutting angle is within the range 118° to 131° but preferably 125° and the outward taper of the bore of the hollow tube starts a short distance preferably 3 mm from the cutting end.

According to a further aspect of the present invention there is provided a wood coring kit comprising a wood coring drill bit as discussed above and a core extraction device for extracting a core located in a cavity in a piece of wood excavated by said coring drill bit, said core extraction device having a shaped cutting end and a handle at an opposite end thereof, said cutting end and said handle being joined by a elongate shaft whereby said cutting end is positioned towards the end of the excavated cavity formed by said coring bit and the handle which is exterior of the cavity is rotated to cut the shank of the core located within the cavity.

BRIEF DESCRIPTION OF THE DRAWINGS

These and other features of the present invention will be more completely understood from the following description of a preferred but non-limiting embodiment of the present invention, which is provided by way of example only. In the following description, reference will be made to the accompanying drawings, wherein:

FIG. 1 is a side view of a drill bit constructed in accordance with the present invention;

FIG. 2 is a schematic sectional view of the drill bit illustrated in FIG. 1;

FIG. 3 depicts the construction of cutting ends of the bodies of the drill bit of FIGS. 1 and 2;

FIG. 4 is an end view of the drill bit of FIGS. 1 and 2, in the direction of the arrow A;

FIG. 5 is a sectional representation of the bodies at AA of FIG. 1;

FIG. 6 is a sectional representation of the bodies at BB of FIG. 1;

FIGS. 7a and 7b are side elevational views of the cutting end of the drill bit at different angular orientations.

DETAILED DESCRIPTION OF THE ILLUSTRATED EMBODIMENT

Figure 8:
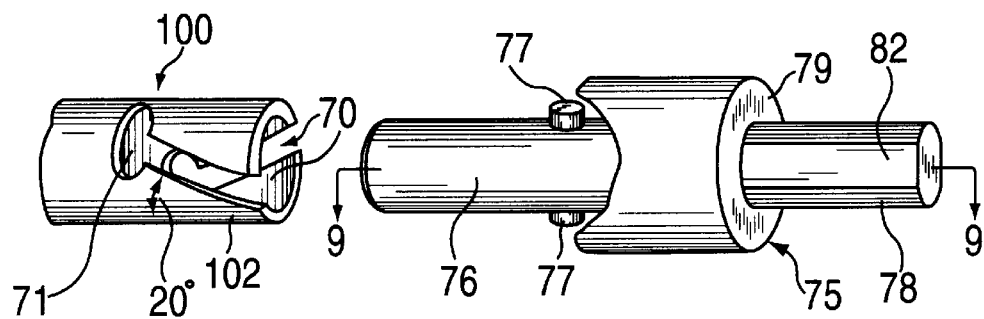
FIG. 8 is an isometric view of a connector adapted to connect the drill bit of the present invention to the chuck of a drill.

The drill bit 100 as illustrated in FIGS. 1 to 7 comprises a tube of tool steel defining a cutting end 101 and mounting end 102. The tube has a bore 103 which progressively increases from B1 at the cutting end 101 of the drill bit to the uniform value of B2, which is the bore diameter for most of the length of the drill bit. This increase in diameter of the bore of the drill bit has been found necessary to prevent the wood core from breaking up within the drill bit. The angle of the taper is not critical, but the taper to the larger bore must be completed within a short distance, D1, and the core must not be too loose within the bore of the drill bit (otherwise the core will break up). A preferred but non-limiting drill bit construction, for obtaining wood cores of diameter 12 mm, has an outside diameter of 22 mm±22 mm, an opening at its cutting end 101 (dimension B1) of 12.7 mm, ±0.5 mm and the bore tapers at about 4°±0.5° over a distance, D1, of 22 mm±2 mm to a diameter (B2) of 14.0 mm±1 mm. Obviously, depending on the core diameter required, the characteristics and dimensions of the corer can be varied—for example—the outside diameter of a pole corer to provide a 7 mm core would be approximately 16 mm.

The outer surface of the drill bit of FIGS. 1 and 2 is machined to form three bodies 10, each of substantially equal width, and equispaced from each other. The bodies 10 are formed as a helix, with the helix angle preferably in the range of from 42° to 48°, and most preferably about 45°.

The grooves between the bodies 10 define flutes 15. The provision of three equally spaced bodies 10 and flutes 15 ensures an even cut by improving stability and reducing wobble. Since the bit has no point or screwed end it is important that the bit initially is placed squarely on the timber. The provision of three equally spaced bodies 10 ensures good stability.

At the cutting end portion (about 65 mm) of the drill bit 100 the leading edge of each body 10 is machined to define an upstanding land 20 between 0.7 mm and 1.4 mm in width. The portion behind the land 20 defines a relief 21. At the front face 11 of each body 10 the leading edge of the body and the land 20 defines a cutting edge 12 terminating as shown in FIG. 4 in a lip 25. The cutting edge 12 of each body 10 is relieved to define a rake angle of 15° to the axis of the drill as shown in FIG. 7*a*.

At the cutting end 101 of the drill bit 100, the bodies 10 terminate in the usual cutting configuration, but with some variations on the cutting configuration parameters. The included angle, θ, of the cutting edges of the cutting configuration in conventional wood drills is normally 118°. In the present invention, the included angle should be increased to up to about 131° but preferably 125° when the corer is to be used with hardwoods, and reduced to about 106°, but preferably about to about 112° when the drill bit is to be used to take cores of soft wood. These variations of the included angles improve the seating of the drill bit when a wood core is being taken. Clearly, unless cores of one type of wood only are to be obtained (for example, when the corers is to be used for testing wooden power poles or telegraph poles), a person taking core samples should carry at least two core drill bits, one for taking cores of soft timbers, one for obtaining core samples of hardwood.

As shown in FIGS. 3 and 7 the lip 25 of each land 20 is inclined rearwardly from the front face of the bit through a lip clearance angle of between 5° and 8° (FIG. 7*a*).

The removal of frass (chips of wood and sawdust) from the wood coring drill bit is an important factor in the efficient use of the drill bit. Two design criteria of the present embodiment facilitate the removal of frass. The first of these criteria is a step-down of about 0.5 mm±0.1 mm in the outer diameter of the drill bit at a distance D2 from the cutting end of the drill bit. The distance D2 is not critical, but experimental work with prototype drill bits has shown that if D2 is about 65 mm±10 mm, then the frass is removed efficiently when a wood core is being taken, and does not jam the drill bit. The second criteria for the efficient removal of frass is the undercutting of the leading faces of the helical lands 20, also for a distance D2, preferable about 65 mm±10 mm, from the cutting end 101 of the drill bit 100. This undercutting means that the shape of the flutes 15 and bodies 10 of the drill bit change after 65 mm from the cutting end 101, from the profile shown in FIG. 5 (a schematic sectional view through a body 10 in the first 65 mm of the drill bit) to the flute and body profile depicted in FIG. 6.

The flutes 15 are shaped to what is known as parabolic flute shape. The flutes have a concave cutting face which is rolled out at the back to reduce clogging. As shown in FIG. 7*a* the base of each flute 15 has a notch of 0.5 mm cut out at the front face. The wall of each flute is also undercut through an approach angle of 25° to 30° at the front as shown in FIG. 7*b* to provide back-away clearance.

The drill bit 100 described above has especially been designed for use with green timber (softwood and hardwoods). The bit may also be used for drywoods such as lighting and telegraph poles. In one option the included point angle of the cutting faces is 118°±3° whilst in another option the angle may be 125°±3°. In that example the O/D is 16 mm and the I/D B2 is 8 mm. The internal taper of the bore 103 starts 3 mm from the front face that has a bore of 6 mm diameter. The bore 103 then tapers outwardly over about 65 mm to the diameter of 8 mm.

A typical wood coring drill bit 100, constructed in accordance with the present invention, will have an overall length of about 305 mm, with the helical bodies and flutes present for about 225 mm. The remaining portion, generally at least 80 mm, includes the mounting end 102 which is furnished with an arrangement whereby the drill bit 100 may be held securely connected to the chuck of a power drill. The power drill (not shown) is essentially a heavy duty petrol driven clutch controlled power drill for use in forests and other remote locations.

Figure 9:
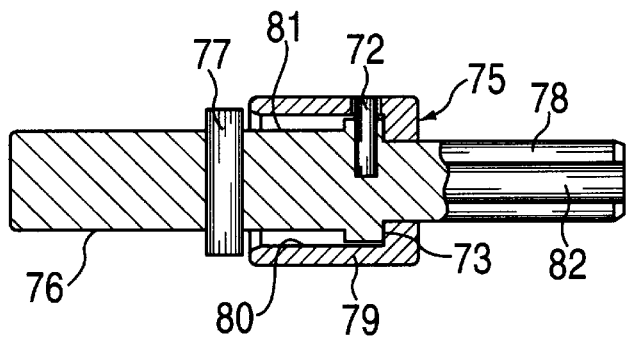
FIG. 9 is a sectional view taken along the lines CC of FIG. 8.

To mount the drill bit 100 on a power drill the arrangement illustrated in FIGS. 8 and 9 is preferred. The mounting end 102 of the drill bit 100 is provided with a pair of complementary slots 70, which extend from the end of the drill bit at an angle φ of say about 20° to its axis, terminating in a T-shaped slot 71, the centre line of which is in a plane orthogonal to the axis of the drill bit. A T-shaped slot 71 is preferable as opposed to a more conventional design of a bayonet fitting so that, when reversing the direction of the drill bit to remove it from the tree or other wood product, the drill bit 100 does not become disengaged from the drill.

The configuration of the mounting end 102 of the drill bit 100 enables the drill bit to be rapidly mounted on (and removed from) a connector 75 comprising a major shaft 76 having (i) a diameter which is a close—but loose—fit within the bore 103 of the drill bit, and (ii) pins or lugs 77 projecting from the shaft 76 and adapted to be engaged by the slots 70 and 71. The shaft 76 is separated from a minor shaft 78 by an annular sleeve 79. The minor shaft 78 is normally retained in the jaws of a drill chuck (not shown) for the entire period within which an operator obtains wood cores.

As shown in FIGS. 8 and 9 the sleeve 79 is held onto the shafts 76 and 78 by a radial pin 72 and a shoulder 73 on the joint between the shafts 76 and 78 that engages one end of the sleeve 79. The internal bore 80 of the sleeve defines an annular gap 81 between the shaft 76 and bore 80. The wall of the corer is a close but sliding fit within the gap 81 to facilitate rotation of the corer to the sleeve 79 and location of the pins 77 in the slots 70 and 71. The minor shaft 78 has flattened sides 82 to improve engagement with the drill chuck.

The connection arrangement, illustrated in FIGS. 8 and 9, enables a drill bit 100 to be connected rapidly to a power drill when a core—or a number of wood cores—are to be obtained, and to be disconnected from the power drill when the drilling is completed. For the period of the drilling, the drill bit is securely mounted on the power drill, so that drilling to obtain a wood core is a relatively undemanding task (physically) and there is little risk of damage to the core as it is created within the drill bit structure.

Various experiments by the inventors in testing the wood corer of the present invention have revealed that the corer has preferable speeds in operation. In particular, it is noted that, for eucalypts, speeds of 300 rpm to 500 rpm provide good core results, whilst for pines, higher speeds of about 800 rpm are better. For a corer suitable for both drywoods and greenwoods, a speed within this range would seem appropriate.

METHOD OF OPERATION

The operator fits the coupling 75 to the drill chuck and fits the corer 100 to the coupling, starts the drill motor and commences drilling.

For the first 5–6 cm of wood the operator should use a firm pushing action—beyond this it is necessary to use a frequent "pecking" action.

The operator should keep the engine at full throttle throughout the operation.

As the corer is withdrawn at each peck to help remove frass, it is important not to totally withdraw the corer but to stop about 5 cm from the point of entry so that the core end is not damaged. The frass should flick out easily. This will become easier with experience. The frequency of the pecking action will vary from wood to wood.

The operator should try and maintain the chosen coring orientation throughout the operation.

when the desired core length is reached (bark-to-bark, bark-to-pith or outer-to-centre of a pole), the operator withdraws the corer from the tree or pole and switches off the motor.

In bark-to-bark sampling, the corer is uncoupled from the drill and the core is dislodged from the corer by pressing the core end at the cutting face with a piece of dowelling or a stick. It is important not to use a metal object as the cutting edge of the corer may be damaged.

In bark-to-pith or outer-to-center sampling, an extraction device is inserted into the excavated area after the corer is withdrawn, pushed in until it reaches the end of the excavated area and then rotated. The cutting piece on the end of the device will sever the core and can then be used to pull out the core.

When the present invention is used to obtain a core sample from a tree, a power pole, a timber beam or pile, the normal procedure after removal of the core is to place a length of dowelling of appropriate diameter (for example, a length of broom handle) within the cavity created by the use of the drill bit, to prevent access by water, pathogens, insects, and other timber-weakening flora or fauna to the timer from which a core has been removed.

Figure 10:
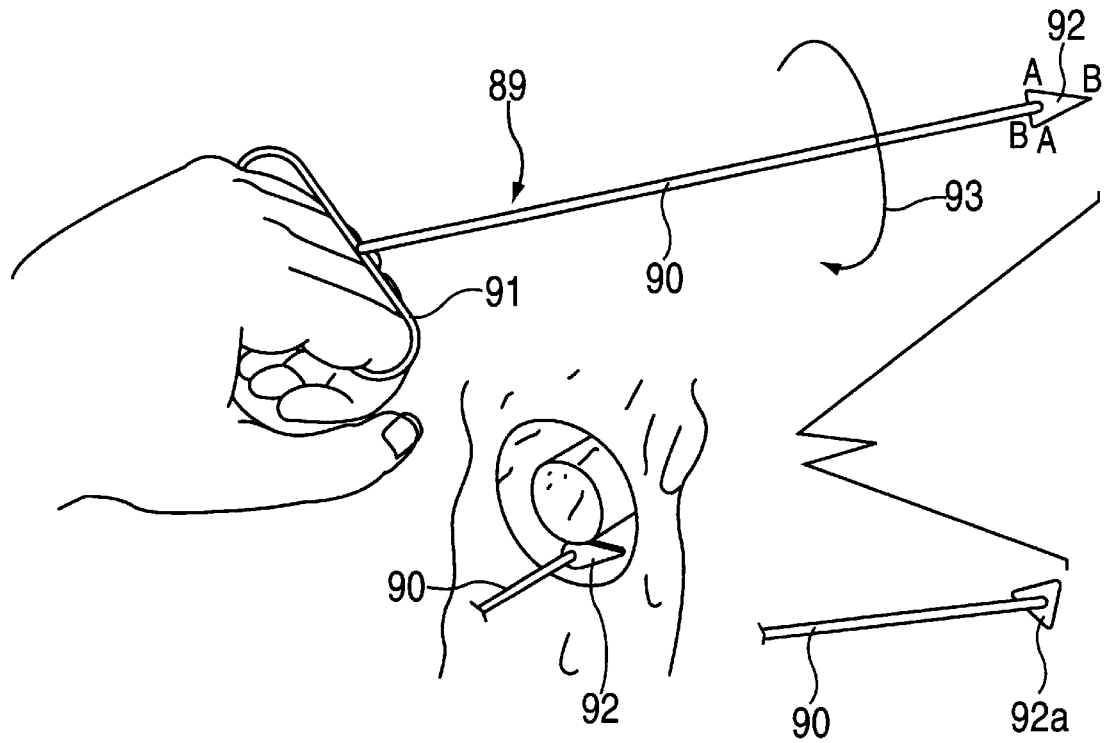
FIG. 10 is an artists impression of a core removal tool illustrating its use.

A typical extraction device 89 suitable for extracting the core from a cavity is shown in FIG. 10, comprising a shaft 90, having a handle 91 at a first end thereof, and a shaped cutting end 92. The cutting end 92 may be of various designs, such as a tear-shape, or a triangular shape 93. Such a device would be required for taking 'bark to pith' cores, wherein, after the corer is withdrawn, the tool 89 is inserted into the excavated cavity left by the corer. The tool 89 is inserted until it reaches the end of the cavity. The tool is then rotated in the direction of arrow 93 to cut the shank of the core being extracted. Preferably, the width of the cutting end, i.e., width AA should not be greater than 4.5 mm and the length of the cutting end, i.e., the length BB is about 6–7 mm.

Figure 11:
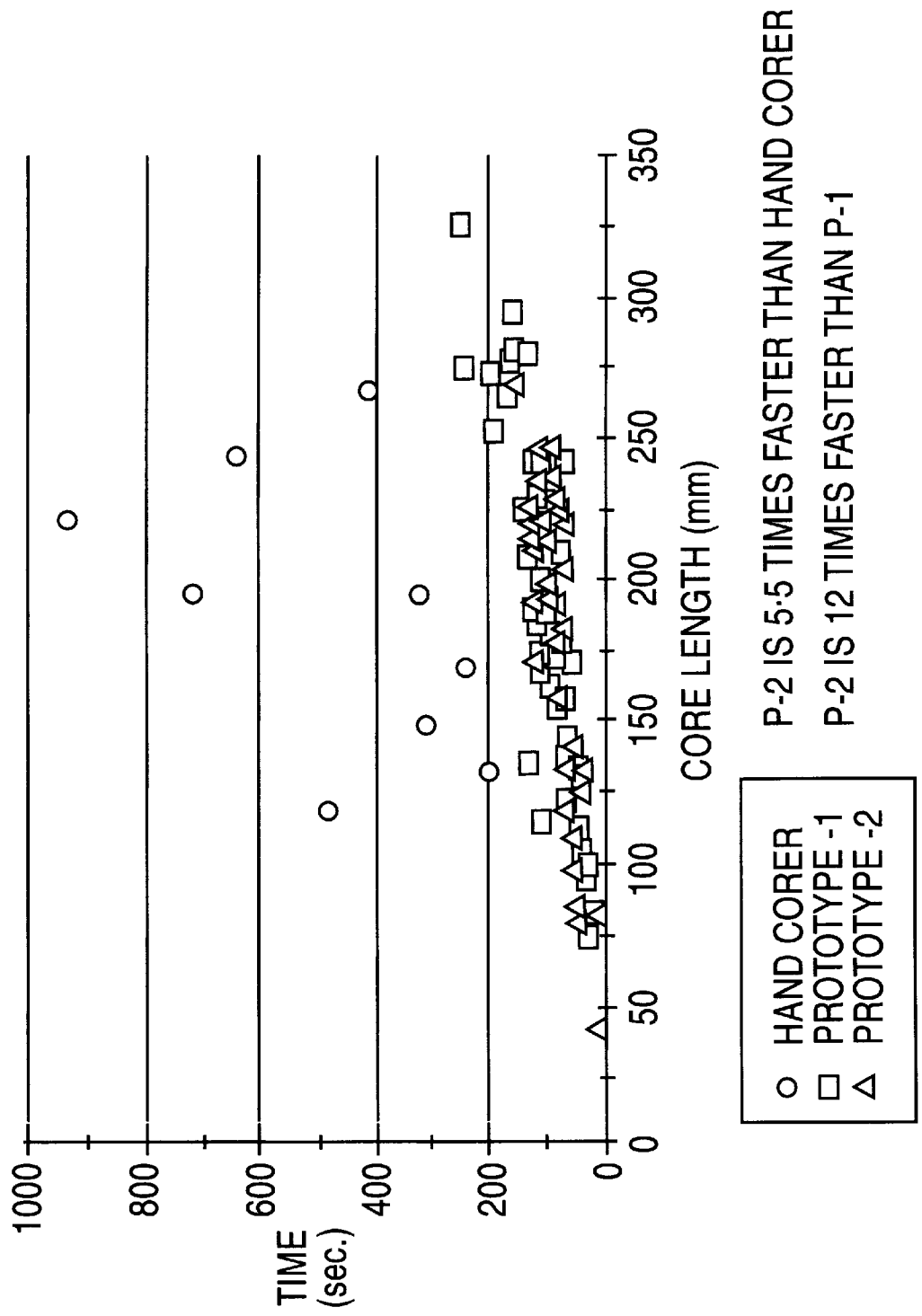
FIG. 11 graphically illustrates data of various trials in coring eucalypt timber.
Figure 12:
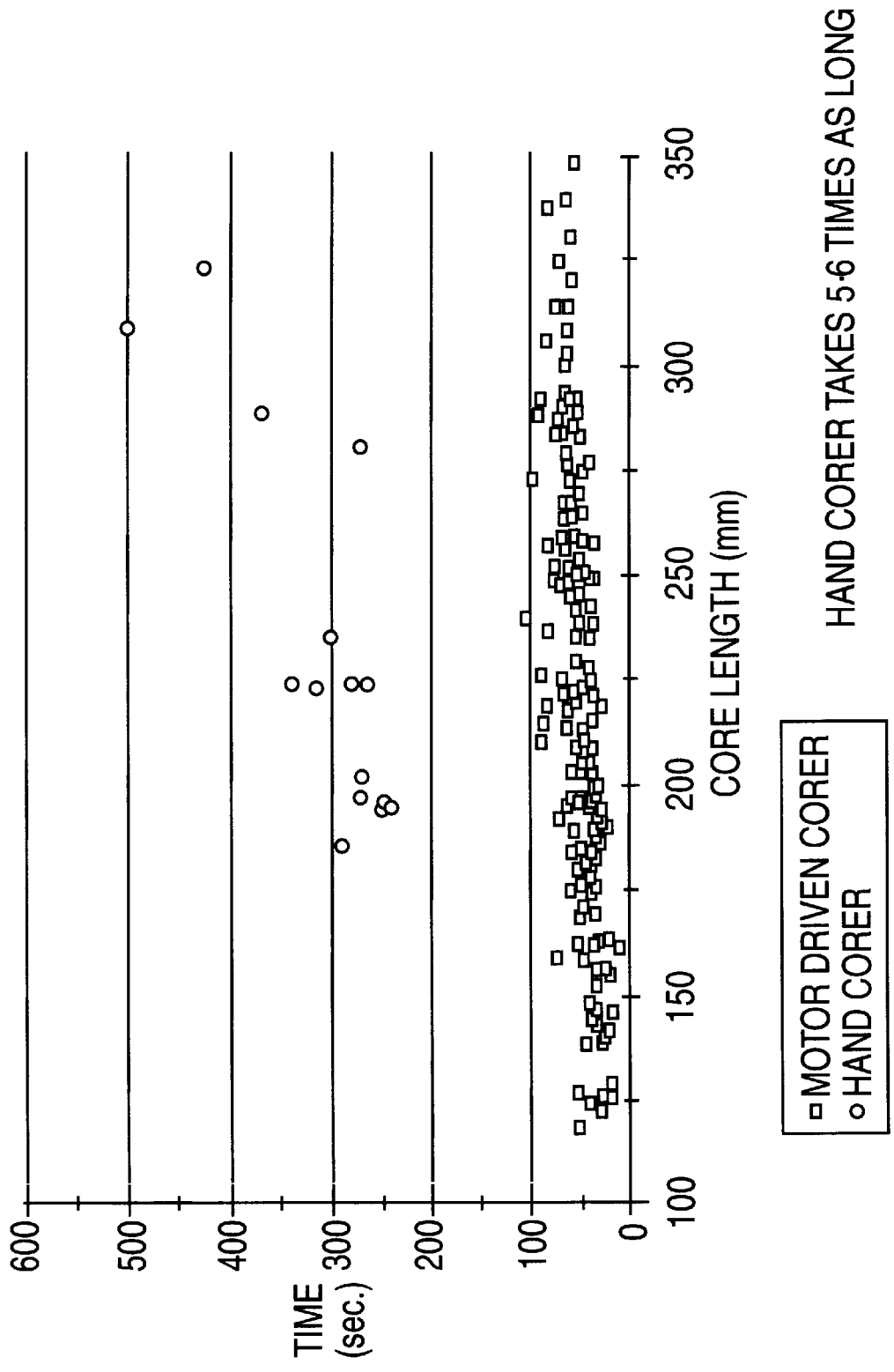
FIG. 12 graphically illustrates data of various trials in coring pine timber, the trees being less than 15 years old.

Various trials have been performed by the inventors. The results of some of such trials are shown in FIGS. 11 and 12 which illustrate how much quicker the corer of this invention operates compared with manual corers.

In the manufacture of a wood coring drill bit manufactured from metal, such as tool steel, a specific heat treatment is preferably utilised, such that the appropriate hardness/elasticity properties are provided. Details of a preferred heat treatment regime are as follows:

Material:

M2 RSS Steel
Heat Treatment Regime

Temperature 1200° C.
Time in furnace - 1 minute 15 seconds
Tempering 2 hours at 560° C.
Cool to room temperature
Temper again - 2 hours at 560° C.
Toughening Tang 1 minute at 880° C.
Oil quench
No temper In a preferred embodiment, the cutting end portion of the wood coring drill bit is coated with titanium nitride (TiN), titanium oxide, titanium dioxide, P.T.F.E., etc, for additional harness/elasticity properties. Such a coating also provides a visual indicator such that, when the bit is being removed from the tree or other wood product, after the coring procedure, the operator may easily identify the proximity and portion of the bit, such that the physical exertion forces may be appropriately adjusted.

It will therefore be appreciated that by the unique design of the drill bit hereinbefore described, a sound core of any suitable size may be clearly and easily removed from any source of wood. It should also be appreciated that whilst this specification describes a drill bit which incorporates several novel features, including the specially designed cutting head, a configuration of an inner bore to ensure the integrity of the core, frass clearing flutes, and the quick (reversible) coupling, these features may be utilised to advantage separately. Their separate and combined use, in any combination, should be considered to be encompassed by the invention as broadly hereinbefore described.

Although a specific embodiment of the present invention has been illustrated and described in this specification, it should be apparent to those familiar with coring tools that variations to, and modifications of, the illustrated exemplary embodiment may be made without departing from the present inventive concept. For example, whilst specific measurements, etc, are hereinbefore mentioned in describing preferred embodiments, variations from those specific measurements, etc, will of course be possible. All such variations and modifications should be considered to fall within the spirit and scope of the invention as broadly described hereinbefore.

We claim:

1. A wood coring drill bit comprising:
    a hollow tube having an internal bore and an exterior with three equally spaced bodies of substantially uniform width extending in a helical manner from a cutting end of said drill bit, said bodies defining three equally spaced flutes between the edges of adjacent bodies, each body comprising
        a land upstanding from a relief at the leading edge of the body, a respective cutting face having an included angle which is within the range of 106° to 131° and associated lip being formed at the end of each body at said cutting end, said lip having a lip clearance angle that is approximately 6°±°1;
    wherein the lands on the bodies extend for an axial distance of about 65 mm±5 mm from said cutting end and the internal bore of the hollow tube is tapered outwardly from or adjacent the cutting end.

2. The wood coring drill bit according to claim 1, wherein the outside diameters of the bodies are stepped down by about 0.5±0.1 mm at a distance of about 65 mm±10 mm from said cutting end.

3. The wood coring drill bit according to claim 1, wherein the taper of the bore of the hollow tube is at an angle of 4°±°1 for distance of 22 mm±2 mm from the cutting end.

4. The wood coring drill bit according to claim 2, wherein the taper of the bore of the hollow tube is at an angle of 4°±°1 for distance of 22 mm±2 mm from the cutting end.

5. The wood coring drill bit according to claim 1, wherein the drill bit is made of tool steel.

6. The wood coring drill bit according to claim 4, wherein a portion of the bit including the cutting end is coated in a material for increased hardness, for reduced friction or a marker to provide a penetration indicator.

7. The wood coring drill bit according to claim 6, wherein the coating materials include titanium nitride, titanium oxide, titanium dioxide, P.T.F.E., or ceramics.

8. The wood coring drill bit according to claim 1, wherein the drill bit is tempered to a desired hardness using a specific heat treatment regime.

9. The wood coring drill bit according to claim 5, wherein the drill bit is tempered to a desired hardness using a specific heat treatment regime.

10. The wood coring drill bit according to claim 1, wherein the end of the tube opposite from cutting end has a pair of diametrically opposed complementary slots which are shaped to permit bayonet type coupling to a connector which is adapted to be held in the chuck of a drill.

11. The wood coring drill bit according to claim 10, wherein the connector comprises a shaft with projecting pins, the shaft locating within the bore of the tube with the pins in the slots, an annular sleeve surrounding one end of said shaft, and a mounting shaft extending from the annular sleeve adapted to be held in the chuck of a drill.

12. A wood coring drill bit for use with soft wood according to claim 1, wherein the included cutting angle is within the range 106° to 118°.

13. A wood coring drill bit for use with hardwood according to claim 1, wherein the included cutting angle is within the range 118° to 131°.

14. A wood coring drill bit for drywood according to claim 1, wherein the included cutting angle is within the range 118° to 131°, and the outward taper of the bore of the hollow tube starts approximately 3 mm from the cutting end.

15. A wood coring drill bit for use with soft wood according to claim 1, wherein the included cutting angle is approximately 112°.

16. A wood coring drill bit for use with hardwood according to claim 1, wherein the included cutting angle is approximately 125°.

17. A wood coring drill bit for drywood according to claim 1, wherein the included cutting angle is approximately 125° and the outward taper of the bore of the hollow tube starts near the cutting end.

18. A wood coring kit comprising:
    I. a wood coring drill bit including:
        A. a hollow tube having an internal bore and an exterior with three equally spaced bodies of substantially uniform width extending in a helical manner from a cutting end of said drill bit, said bodies defining three equally spaced flutes between the edges of adjacent bodies, each body comprising a land upstanding from a relief at the leading edge of the body, a respective cutting face having an included angle which is with the range of 106° to 131° and associated lip being formed at the end of each body at said cutting end, said lip having a lip clearance angle that is approximately 6°±°1;
        B. wherein the lands on the bodies extend for an axial distance of about 65 mm±5 mm from said cutting end and the internal bore of the hollow tube is tapered outwardly from or adjacent the cutting end; and
    II. a core extraction device for extracting a core located in a cavity in a piece of wood excavated by said coring drill bit, wherein said core extraction device has a shaped cutting end and a handle at an opposite end thereof, said cutting end and said handle are joined by a elongate shaft whereby said cutting end is positioned towards the end of the excavated cavity formed by said coring bit and the handle which is exterior of the cavity is rotated to cut the shank of the core located within the cavity.

* * * * *